US00PP21298P2

(12) United States Plant Patent
Giesen

(10) Patent No.: US PP21,298 P2
(45) Date of Patent: Sep. 14, 2010

(54) *TORENIA* PLANT NAMED 'TOR BULE'

(50) Latin Name: *Torenia fournieri*
Varietal Denomination: Tor Bule

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 160 days.

(21) Appl. No.: 12/313,475

(22) Filed: Nov. 20, 2008

(51) Int. Cl.
*A01H 5/00* (2006.01)

(52) U.S. Cl. ..... Plt./487

(58) Field of Classification Search ..... Plt./487
See application file for complete search history.

(56) References Cited

U.S. PATENT DOCUMENTS

PP10,843 P * 3/1999 Tamura et al. ..... Plt./487
PP17,009 P2 * 8/2006 Danziger ..... Plt./487
PP17,024 P3 * 8/2006 Danziger ..... Plt./487

* cited by examiner

*Primary Examiner*—Wendy C. Haas
(74) *Attorney, Agent, or Firm*—S. Matthew Edwards

(57) ABSTRACT

A new *Torenia* plant named 'Tor Bule' particularly distinguished by bi-colored, violet-blue and pale blue flowers, medium to grass-green foliage, triangular leaves, moderately vigorous growth, freely branching with relatively short internodes, bushy, semi-upright to later semi-trailing, and about medium sized plant habit.

1 Drawing Sheet

Latin name of the genus and species of the plant claimed *Torenia fournieri.*

Varietal denomination 'Tor Bule'.

BACKGROUND OF THE NEW PLANT

The present invention comprises a new *Torneia*, botanically known as *Torenia fournieri,* and hereinafter referred to by the variety name 'Tor Bule.'

'Tor Bule' is a product of a planned breeding program. The new cultivar originated from a hybridization made in July 2004 in Andijk, Netherlands.

The female parent was an unpatented, proprietary *Torenia* plant designated 'TO05-4-1', having blue flower color. 'TO05-4-1' has smaller flowers and larger leaves than 'Tor Bule.'

The male parent of 'Tor Bule' was an unpatented proprietary *Torenia* plant designated 'TO05-6-2,' having blue and white flower color. 'TO05-6-2' has a less upright plant habit than 'Tor Bule.'

The resulting seeds were sown in December 2004. 'Tor Bule' was selected as one flowering plant within the progeny of the stated cross in March 2005 in a controlled environment in Andijk, Netherlands.

The first act of asexual reproduction of 'Tor Bule' was accomplished when vegetative cuttings were taken from the initial selection in the summer of 2005 in a controlled environment in Andijk, Netherlands.

Horticultural examination of plants grown from cuttings of the plant initiated in the spring of 2006 in Andijk, Netherlands, and in Hillscheid, Germany, and continuing thereafter, has demonstrated that the combination of characteristics as herein disclosed for 'Tor Bule' are firmly fixed and are retained through successive generations of asexual reproduction.

'Tor Bule' has not been observed under all possible environmental conditions. The phenotype may vary significantly with variations in environment such as temperature, light intensity and day length.

Plant Breeders' Rights for this cultivar were applied for in Canada on Dec. 24, 2007 and with the European Union on Jul. 21, 2008. 'Tor Bule' has not been made publicly available more than one year prior to the filing of this application.

DESCRIPTION OF DRAWING

This new *Torenia* plant is illustrated by the accompanying photograph which shows blooms, buds, and foliage of the plant in full color. The colors shown are as true as can be reasonably obtained by conventional photographic procedures. The photograph, taken in mid July 2008, is of three about 4-5 months old plants planted into a 25 cm diameter basket and grown in a greenhouse with natural light in a spring to early summer trial setting.

DETAILED BOTANICAL DESCRIPTION

The measurements were taken in Hillscheid, Germany, on May 24, 2008 on 10 week old plants that were growing in a greenhouse. The culture of these plants had started with planting of rooted cuttings into 12 cm pots in early March 2008, which were pinched shortly after that to enhance branching.

Color chart used: The Royal Horticultural Society Colour Chart (R.H.S.), 2001.

BRIEF SUMMARY OF INVENTION

The following observations, measurements, and comparisons describe plants grown indoors and outdoors in Andijk, Netherlands, and in Hillscheid, Germany. The following traits have been repeatedly observed and are determined to be basic characteristics of the new variety. The combination of these characteristics distinguishes this *Torenia* as a new and distinct variety:

1. Bi-colored flowers, deep violet-blue with pale blue throat
2. Medium green to grass-green foliage, triangular leaves 3. About medium growth vigor in combination with relatively short internodes and well branching
4. Initially ascending and bushy, later low, mounding to semi-trailing plant habit

COMPARISON WITH COMMERCIAL CULTIVARS

'Tor Bule' differs from the commercial cultivar 'Summer Wave Large Blue' (U.S. Plant Pat. No. 10,843) in that 'Tor Bule' has a darker blue flower color, more branches with shorter internodes, resulting in a bushier and less trailing plant habit.

Plant:

*Growth and habit.*—Moderately vigorous growth habit; dense and freely branched with relatively short internodes.

*Height.*—6-10 cm (from top of soil) for 10 week old plants.

*Width (diameter).*—22-28 cm.

*Number of branches.*—About 15.

*Time to produce a finished flowering plant.*—About 8-10 weeks for a 12 cm pot.

*Outdoor plant performance.*—Used for hanging baskets, as patio planters, in mixed container plantings.

*Time to initiate and develop roots.*—21-24 days at 20-24 degrees C.

*Root description.*—Fibrous and freely branching.

Stem:

*Characteristics.*—Cross section square, with somewhat strengthened edges, on flowering stems usually one flower and a branch stem emerge on every node.

*Stem length.*—About 18-25 cm.

*Diameter.*—3-4 mm.

*Internode length.*—About 2.5-3.5 cm.

*Color.*—RHS 144B, no anthocyanin.

*Texture.*—Covered with hair, hirsute, mainly along the edges.

Foliage:

*Arrangement.*—Opposite, decussate.

*Shape.*—Deltoid (triangular).

*Apex.*—Acute.

*Base.*—Truncate or slightly cordate.

*Margin.*—Crenate, relatatively shallow.

*Leaf length.*—Up to 5.5 cm.

*Leaf width.*—Up to 4.0 cm.

*Immature leaf, color upper surface.*—RHS 143A to 143B.

*Immature leaf, color lower surface.*—From RHS 138B to 143C.

*Mature color upper surface.*—RHS 137B.

*Mature color lower surface.*—RHS 139C.

*Venation type.*—Pinnate.

*Venation color.*—RHS 144B on lower side, indistinct on upper surface.

*Texture.*—Glabrous.

Petiole:

*Length.*—0.2-0.6 cm.

*Petiole width.*—2 mm.

*Petiole color.*—RHS 143A, lower side RHS 144B.

*Texture.*—Sparse hair.

Inflorescence:

*Blooming habit.*—Continuous through the growing season from spring to fall.

*Type of inflorescence.*—Solitary flowers emerge from upper nodes of the stem.

*No of flowers per stem.*—Most often 2-4 open flowers and additional buds.

*Lastingness of individual blooms on the plant.*—3-5 days, depending on temperature.

*Fragrance.*—None.

Flower:

*Corolla type and shape.*—Single-type, zygomorphic; lower part funnel-shaped, 5 petals fused at the base, petal lobes opening outwards, 2 mainly fused lobes forming the upper lip, 2 lateral and the lower lobe forming the lower lip.

*Corolla, total length.*—2.8-3.2 cm.

*Tube length.*—2.5-2.8 cm.

*Tube width.*—0.8-1.0 cm.

*Flower 'face' diameter.*—3.5-4.0 cm in length, 3.2 cm in width.

*Color upper surface.*—RHS N89A on lateral lobes.

*Color at margin.*—RHS N88A-N88B.

*Color towards center of flower.*—RHS 91B to 91C.

*Color lower surface.*—At margin RHS N88B or 93B, fading towards base.

*Marking on lower lip.*—Light yellow stripe, RHS 5C.

Petal (lobes):

*Apex.*—Rounded.

*Base.*—Fused.

*Margin.*—Entire, somewhat wavy.

*Texture.*—Glabrous.

*Upper lobe, length (from the funnel opening).*—1.5-1.8 cm.

*Upper lobe, width.*—About 2.8 cm.

*Lateral lobes, length (from the funnel opening).*—1.0-1.2 cm.

*Lateral lobes, width.*—1.8 cm.

*Lower lobe, length (from the funnel opening).*—1.5-1.8 cm.

*Lower lobe, width.*—1.7-1.9 cm.

Flower bud (just before opening):

*Shape.*—More or less tubular.

*Diameter.*—0.7-0.8 cm.

*Length.*—2.5-2.8 cm.

*Color (at tight bud).*—About RHS N88A.

Calyx:

*Shape.*—5 sepals, mostly fused, winged along the edges, forming a 2-lipped tube around the base of the flower, tips opening outwards.

*Sepal color.*—RHS 143C, in between part RHS 144C.

*Length.*—Up to 2 cm.

*Diameter of calyx tube.*—About 0.5 cm.

*Apex.*—Tips acuminate.

*Base.*—Fused.

*Texture.*—Short bristle like hairs along the edges.

Pedicels:

*Color.*—RHS 143C or 144B.

*Length.*—Approximately 1.5-2.0 cm.

*Diameter.*—1.5-2 mm.

*Texture.*—Smooth, glabrous or almost glabrous.

Reproductive organs:

*Stamens.*—Quantity: 4, 1$^{st}$ pair epipetal with short filaments and connate, 2$^{nd}$ pair solitary with longer filaments. Filament, color: Pale violet, RHS 91C. Length: 1$^{st}$ pair 0.5 cm, 2$^{nd}$ pair about 1.5 cm. Diameter: 1 mm. Anther color: RHS 91C. Pollen amount: Sparse. Pollen color: Cream, RHS 158C.

*Pistil.*—Quantity per flower: One. Length: Approximately 2.5 cm. Stigma color: RHS 76B-C. Style color: RHS 76B. Ovary shape: Elliptical. Ovary length: 2-3 mm. Ovary color: RHS 143B, green.

Fruit and seed set: No seed set observed.

Disease/pest resistance: Resistance and susceptibility typical for the species, no special observations made.

What is claimed is:

1. A new and distinct variety of *Torenia* plant named 'Tor Bule,' substantially as illustrated and described herein.

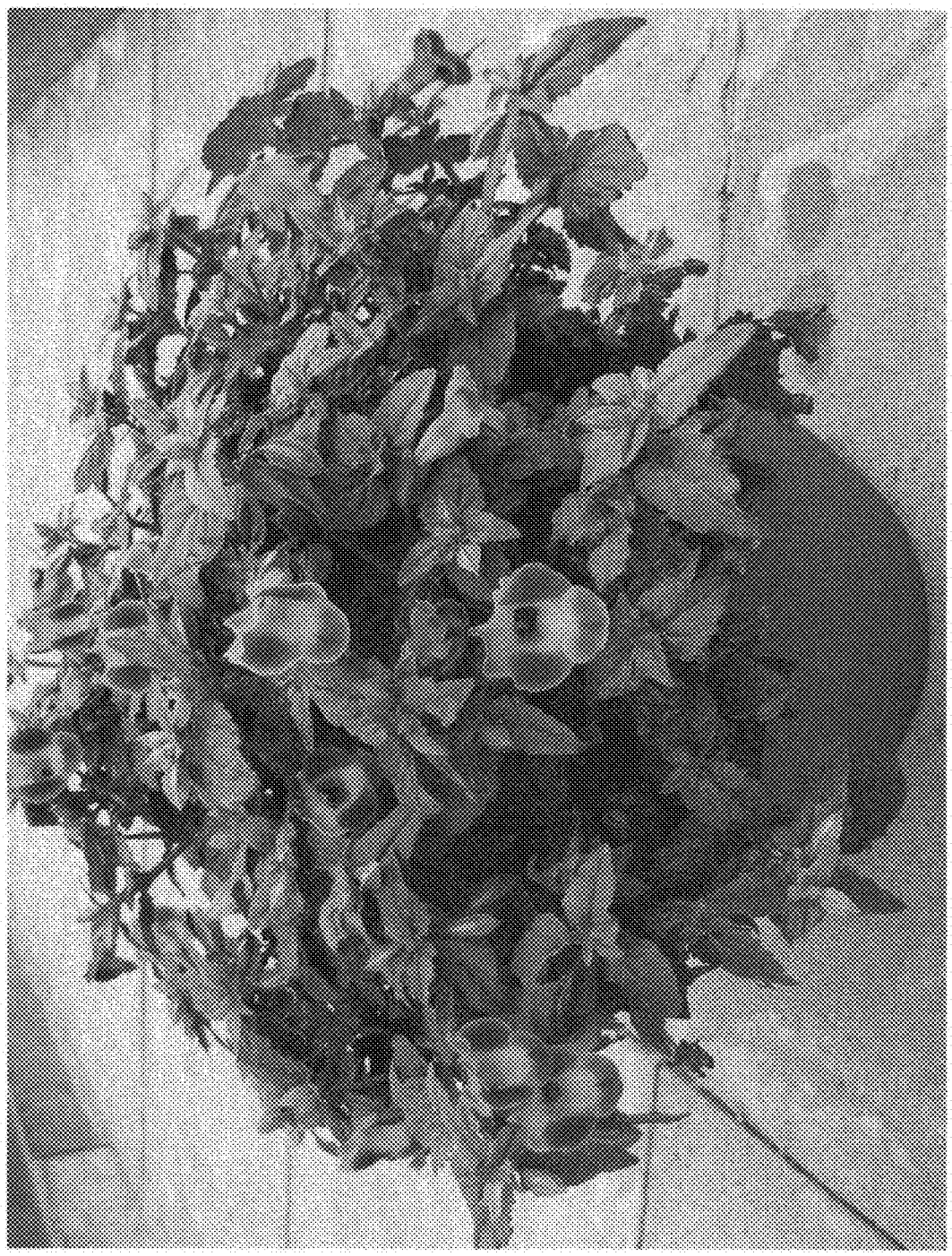

* * * * *